United States Patent [19]

Santangelo et al.

[11] Patent Number: 5,519,054

[45] Date of Patent: May 21, 1996

[54] PHARMACEUTICAL COMPOSITIONS CONTAINING N-ACETYL-CYSTEINE DERIVATIVES USEFUL FOR THE TREATMENT OF CATARACT

[75] Inventors: Francesco Santangelo, Milan; Giorgio Bertolini, Sesto San Giovanni; Franco Pellacini, Milan, all of Italy; Luciano Soldati, Agra, Switzerland; Annibale Gazzaniga, Rescaldina; Cesare Casagrande, Arese, both of Italy

[73] Assignee: Zambon Group S.p.A., Milan, Italy

[21] Appl. No.: 971,577

[22] Filed: Nov. 5, 1992

Related U.S. Application Data

[62] Division of Ser. No. 836,885, Feb. 19, 1992, abandoned.

[30] Foreign Application Priority Data

Feb. 21, 1991 [IT] Italy ................................ MI91A0456

[51] Int. Cl.$^6$ ................................................. A61K 31/215
[52] U.S. Cl. ........................................... 514/529; 514/912
[58] Field of Search ....................... 514/538, 560, 514/529, 912

[56] References Cited

FOREIGN PATENT DOCUMENTS

| | | |
|---|---|---|
| 0744952 | 1/1969 | Belgium . |
| 0901885 | 1/1985 | Belgium . |
| 0276317 | 3/1987 | European Pat. Off. . |
| 0300100 | 1/1989 | European Pat. Off. . |
| 0004619 | 2/1965 | France . |
| 2651129 | 3/1991 | France . |
| 0092315 | 7/1980 | Japan . |
| 049879 | 11/1981 | Japan . |
| 700494 | 2/1980 | South Africa . |

OTHER PUBLICATIONS

Chemical Abstract 109:93608m (1988). Sato et al.
Kahns, et al "Prodrugs As Drug Delivery Systems; 107; Synthesis and Chemical and Enzymatic Hydrolysis Kinetics of Various Mono– and Diester Prodrugs of N–Acetylcysteine," *International Journal of Pharmaceutics,* 62, (1990) pp. 193–205.

"An in Vitro Model for Determination of Drug Permeability Through the Cornea." *Acta Pharmaceutics* 22, (1985) pp. 335–342.

Camber, et al "Influence of Some Preservatives on the Corneal Permeability of Pilocarpine and Dexamethasone, in Vitro," *International Journal of Pharmaceutics* 39, (1987) pp. 229–234.

*The Merck Index* 11th Ed., "Encyclopedia of Chemicals, Drugs, and Biologicals," No. 82, Acetyleystine (1989) p. 14.

Chemical Abstract No. 86:115832 vol. 86, (1977) p. 99.

Derwent File Supplier, *Derwent Publications Ltd*, JP–A–56 147,715, (1991).

Jose Ferrer, et al "Age–Related Changes in Glutathione Synthesis in the Eye Lens" *The Biochemical Journal* vol. 269, No. 2, (1990) pp. 531–534.

Anne H. Kahns et al "Prodrugs as Drug Delivery Systems. 1–7. Synthesis and Chemical and Enzymatic Hydrolysis Kinetics of Various Mono–and Diester Prodrugs of N–Acetylcysteine" *International Journal of Pharmaceutics* vol. 62 Nos. 2, 3, (1990) pp. 193–205.

Chemical Abstract No. 63608M, vol. 109, (1988) p. 774.

Kahns et al. Internal. J. Pharmaceutics, 62, 100 2, 3, 1990, p. 193.

Design of Biopharmaceutical Properties Through Prodrugs and Analogs. (1978), Roche.

*Primary Examiner*—Zohreh Fay
*Attorney, Agent, or Firm*—Watson Cole Stevens Davis

[57] ABSTRACT

Pharmaceutical compositions for the treatment of cataract containing N-acetyl-L-cysteine derivatives of formula

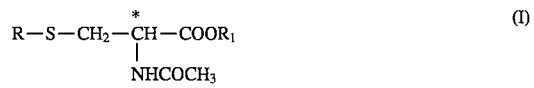

(wherein R and $R_1$ have the meanings reported in the specification) are described.

1 Claim, No Drawings

PHARMACEUTICAL COMPOSITIONS CONTAINING N-ACETYL-CYSTEINE DERIVATIVES USEFUL FOR THE TREATMENT OF CATARACT

This is a Divisional of application Ser. No. 07/836,885, filed Feb. 19, 1992 now abandoned.

Priority of foreign application No. MI91A000456, filed Feb. 21, 1991 in Italy is claimed under 35 USC §119.

The present invention relates to pharmaceutical compositions for the treatment of cataract and, more particularly, it relates to pharmaceutical compositions containing N-acetyl-L-cysteine derivatives. Cataract is a disease of the eye characterized by a loss of transparency of the lens and it may be generally due to many causes but, more commonly, it is associated with aging.

Several anti-cataract compounds have been described in the literature however, as far as we know, they have been never developed for the therapeutic use so much so that the surgical treatment still results to be the more common therapy for cataract.

Among the known compounds, for example, N-acetyl-cysteine (Merck Index XI Ed., No. 82, page 14) whose anti-cataract activity is described in the Japanese patent application No. 56/147715 (Senju Seyaku K.K.-Derwent Accession Number 81-95880D/52) may be cited. However, for the treatment of cataract, N-acetyl-L-cysteine can be administered only by systemic route, that is orally or by injection administration, being inactive when it is topically administered to the eye.

The systemic treatment with drugs which have to operate in the eye shows a lot of disadvantages because it generally does not ensure the reaching of therapeutically effective amounts of active ingredient in the action site, unless very high doses are used.

We have now found prodrugs of N-acetyl-L-cysteine which are active in the treatment of cataracts and which can also be administered by topical route.

Therefore, object of the present invention is a pharmaceutical composition for the treatment of cataract containing a therapeutically effective amount of a compound of formula

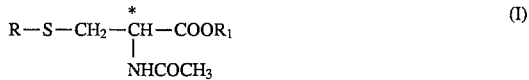

wherein

R is a hydrogen atom or a group of formula $R_2CO$ in which $R_2$ is a linear or branched $C_1$–$C_4$ alkyl group, a $C_1$–$C_3$ dialkylamino group, a $C_1$–$C_3$ alkoxy group optionally substituted by a phenyl or a phenyl;

$R_1$ is a linear or branched $C_1$–$C_3$ alkyl group or a benzyl;

the carbon atom marked by an asterisk has the configuration of L-cysteine;

together with a suitable carrier.

The compounds of formula I are known. In particular, the compounds of formula I wherein R is a hydrogen atom have been described in the South African patent No. 70/494 (Bristol-Myers Co.) as useful for inhibiting the formation of urinary calculi; the compounds of formula I wherein $R_2$ is a linear or branched $C_1$–$C_4$ alkyl group or a phenyl and $R_1$ is a linear or branched $C_1$–$C_3$ alkyl group have been already described as mucolytic agents in the French patent No. 4619M (M. P. Wirth); the compounds of formula I wherein R is a hydrogen atom or a group of formula $R_2CO$ in which $R_2$ is a phenyl and $R_1$ is a benzyl have been described in Kahns et al., Int. J. Pharm., 62, 193–205, (1990).

The compounds of formula I wherein $R_2$ is a $C_1$–$C_3$ dialkylamino group or a $C_1$–$C_3$ alkoxy group are known [see for example Hubbell et al., J. Agric. Food Chem., 25(2), 404–13, (1977)-C.A. 86:115832r] or they can be prepared by known methods from the corresponding esters of formula I wherein R is a hydrogen atom.

Illustratively, a general scheme for the preparation of the compounds of formula I wherein R is different from hydrogen consists in the acylation of the corresponding mercapto derivative (I—R=H) with a suitable acylating agent of formula

wherein $R_2$ has the already reported meanings and X is a chlorine or bromine atom or, when $R_2$ is alkyl, may also be an $R_2COO$ group.

The acylation reaction is generally carried out in a solvent and in the presence of a base according to conventional techniques.

It is clear that, alternatively, another general scheme for the preparation of the compounds of formula I consists in the esterification of the corresponding acids of formula

wherein R has the already reported meanings.

The compounds of formula III are known too (above cited South African patent No. 70/494) or they can be prepared by known methods starting from N-acetyl-L-cysteine.

The compounds of formula I are useful for the treatment of cataract and, in particular, for the topical treatment because, after administration in the eye and transcorneal permeability, they release N-acetyl-L-cysteine.

The anti-cataract activity of the compounds of formula I has been determined by in vitro evaluation tests of the transcorneal permeability (see example 8) as well as of the release of N-acetyl-L-cysteine at the action-site.

The compounds of formula I show a remarkable corneal perfusion ability.

Furthermore, after the transcorneal permeability, they rapidly release N-acetyl-L-cysteine which so reaches therapeutically useful concentrations at the action-site within a short time.

In fact, in the in vitro evaluation tests of corneal perfusion ability, high amounts of hydrolyzed compound are detectable just after transcorneal permeability.

As already underlined, N-acetyl-L-cysteine as such cannot act as an anti-cataract drug by topical administration because it is not able to cross the cornea (see example 8).

For the practical use in therapy, the compound of formula I can be administered in the form of pharmaceutical compositions such as tablets, granulates, solutions and preferably in the form of ophthalmic topical compositions such as eye drops, creams, ointments, suspensions, gels or ocular inserts.

The topical pharmaceutical compositions object of the invention can contain pharmaceutical excipients suitable for the ophthalmic administration in addition to the compounds of formula I.

Examples of suitable excipients are carriers such as water, olive oil, paraffin jelly, paraffin oil and lanolin to which further excipients such as, for example, isotonicity agents, buffering agents, antiseptic agents, antimycotic agents, antioxidant agents, wetting agents, thickening agents and surfactants may be added.

Specific examples of ocular inserts are bioerodible hydroxypropyl-cellulose inserts.

In order to better illustrate the present invention, the following examples are now given.

EXAMPLE 1

Preparation of S-isobutyryl-N-acetyl-L-cysteine Ethyl Ester

Pyridine (85.7 ml; d=0.982; 1.064 moles) and, then, dropwise, a solution of isobutyryl chloride (48.34 ml; d=1.017; 0.452 moles) in chloroform (95 ml) were added to a solution of N-acetyl-L-cysteine ethyl ester (50 g; 0.261 moles) in chloroform (460 ml), under nitrogen and by keeping the temperature at about 30° C.

The reaction mixture was kept under stirring at room temperature overnight, then poured into a mixture of water (250 ml) and concentrated hydrochloric acid (85 ml).

After separation of the phases, the organic phase was washed with 10% hydrochloric acid, twice with water, with a 5% aqueous sodium bicarbonate solution (2×250 ml) and, then, with water again.

After drying on sodium sulfate and evaporation of the solvent, a crude oil was obtained and chromatographed on silica gel (eluent ethyl acetate:hexane=8:2).

By crystallization of the resultant solid from diisopropyl ether, pure S-isobutyryl-N-acetyl-L-cysteine ethyl ester (54.6 g) was obtained.

$[\alpha]_D^{20}$=−20.4° (c=1%, methanol). m.p. 65°–66° C. $^1$H-NMR (200 MHz, CDCl$_3$): δ (ppm): 6.24 (d, 1H, J$_{HH}$=7.8 Hz, NH); 4.80–4.71 (dt, 1H, J$_{HH}$=7.8 Hz, J$_{HH}$=5.5 Hz, C$\underline{H}$—CH$_2$); 4.27–4.05 (m, 2H, C$\underline{H}_2$—CH$_3$); 3.32 (d, 2H, J$_{HH}$32 5.5 Hz, CH$_2$—CH); 2.72 [dq, 1H, J$_{HH}$=7.0 Hz, C$\underline{H}$(CH$_3$)$_2$]; 1.97 (s, 3H, CH$_3$CO); 1.26 (t, 3H, J$_{HH}$= 7.2 Hz, C$\underline{H}_3$CH$_2$); 1.15 [d, 6H, J$_{HH}$=7.0 Hz, (C$\underline{H}_3$)$_2$CH].

EXAMPLE 2

Preparation of S-isobutyryl-N-acetyl-L-cysteine Isopropyl Ester

Pyridine (78.5 ml; d=0.982; 0.974 moles) and, then, dropwise, a solution of isobutyryl chloride (42 ml; d=1.017; 0.413 moles) in chloroform (100 ml) were added to a solution of N-acetyl-L-cysteine isopropyl ester (50 g; 0.243 moles) in chloroform (430 ml), under nitrogen and by keeping the temperature at about 30° C.

The reaction mixture was kept under stirring at room temperature overnight, then poured into a mixture of water (250 ml) and concentrated hydrochloric acid (85 ml).

After separation of the phases, the organic phase was washed with 10% hydrochloric acid, twice with water, with a 5% aqueous sodium bicarbonate solution and, then, with water again.

After drying on sodium sulfate and evaporation of the solvent, a crude oil was obtained and chromatographed on silica gel (eluent ethyl acetate:hexane=7:3).

By crystallization of the resultant solid from hexane, pure S-isobutyryl-N-acetyl-L-cysteine isopropyl ester (40 g) was obtained.

$[\alpha]_D^{20}$=−20.8° (c=1%, methanol). m.p. 59°–59.5° C. $^1$H-NMR (200 MHz, CDCl$_3$): δ (ppm): 6.22 (bs, 1H, NH); 5.00 (m, 1H, COOCH); 4.77–4.68 (m, 1H, C$\underline{H}$—CH$_2$); 3.38–3.23 (m, 2H, CH—C$\underline{H}_2$); 2.72 (m, 1H, SCOCH); 1.96 (s, 3H, COCH$_3$); 1.23 [d, 6H, J$_{HH}$=6.2 Hz, COOCH(C$\underline{H}_3$)$_2$]; 1.15 [d, 6H, J$_{HH}$=7.0 Hz, SCOCH(C$\underline{H}_3$)$_2$].

EXAMPLE 3

Preparation of S-propionyl-N-acetyl-L-cysteine Ethyl Ester

Pyridine (84.2 ml; d=0.982; 1.045 moles) and, then, dropwise, a solution of propionyl chloride (38.8 ml; d=1.059; 0.444 moles) in chloroform (95 ml) were added to a solution of N-acetyl-L-cysteine ethyl ester (50g; 0.216 moles) in chloroform (460 ml), under nitrogen and by keeping the temperature at about 30° C.

The reaction mixture was kept under stirring at room temperature overnight, then poured into a mixture of water (250 ml) and concentrated hydrochloric acid (85 ml).

After separation of the phases, the organic phase was washed with 10% hydrochloric acid, twice with water, with a 5% aqueous sodium bicarbonate solution and, then, with water again.

After drying on sodium sulfate and evaporation of the solvent, a semi-solid crude was obtained and chromatographed on silica gel (eluent ethyl acetate:hexane=8:2).

By crystallization of the resultant solid from diisopropyl ether, pure S-propionyl-N-acetyl-L-cysteine ethyl ester (20.1 g) was obtained.

$[\alpha]_D^{20}$=−28.7° (c=1%, methanol). m.p. 49°–50° C. $^1$H-NMR (200 MHz, CDCl$_3$): δ (ppm): 6.28 (bs, 1H, NH); 4.80–4.70 (m, 1H, CH); 4.16 (q, 2H, J$_{HH}$=7.1; COOC$\underline{H}_2$CH$_3$); 3.41–3.24 (m, 2H, CH$_2$S); 2.54 (q, 2H, J$_{HH}$=7.5 Hz, SCOC$\underline{H}_2$CH$_3$); 1.97 (s, 3H, COCH$_3$); 1.25 (t, 3H, J$_{HH}$=7.1 Hz, COOCH$_2$C$\underline{H}_3$); 1.13 (t, 3H, J$_{HH}$=7.5 Hz, SCOCH$_2$C$\underline{H}_3$).

EXAMPLE 4

Preparation of S-pivaloyl-N-acetyl-L-cysteine Ethyl Ester

Pyridine (68.5 ml; d=0.982; 0.85 moles) and, then, dropwise, a solution of pivaloyl chloride (44.6 ml; d=0.98; 0.355 moles) in chloroform (75 ml) were added to a solution of N-acetyl-L-cysteine ethyl ester (40 g; 0.209 moles) in chloroform (370 ml), under nitrogen and by keeping the temperature at about 30° C.

The reaction mixture was kept under stirring at room temperature overnight, then poured into a mixture of water and concentrated hydrochloric acid (70 ml).

After separation of the phases, the organic phase was washed with 10% hydrochloric acid, twice with water, with a 5% aqueous sodium bicarbonate solution and, then, with water again.

After drying on sodium sulfate and evaporation of the solvent, a semi-solid crude was obtained and chromatographed on silica gel (eluent ethyl acetate:hexane=75:25) giving pure S-pivaloyl-N-acetyl-acetyl-L-cysteine ethyl ester as an oil.

$[\alpha]_D^{20}$=−15.6° (c=1%, methanol). $^1$H-NMR (200 MHz, CDCl$_3$): δ (ppm): 6.20 (bs, 1H, NH); 4.80–4.71 (m, 1H, CH); 4.27–4.05 (m, 2H, C$\underline{H}_2$CH$_3$); 3.31 (d, 2H, J$_{HH=5.5}$ Hz, CH$_2$S); 1.97 (s, 3H, COCH$_3$); 1.26 (t, 3H, J$_{HH}$=7.1 Hz, CH$_2$C$\underline{H}_3$); 1.20 [2, 9H, C(C$\underline{H}_3$)$_3$].

EXAMPLE 5

Preparation of S-(N,N-dimethylaminocarbonyl)-N-acetyl-L-cysteine Methyl Ester Dimethylcarbamoyl chloride (2.76 ml; 30 mmoles) and was added to a solution of N-acetyl-L-cysteine methyl ester (3.54 g; 20 mmoles) and pyridine (4.02 ml; 50 mmoles) in chloroform (35 ml) at room temperature.

The reaction mixture was heated under reflux for 2 hours, then, washed with a diluted hydrochloric acid solution and with water.

After drying on sodium sulfate and evaporation of the solvent, a crude was obtained and purified by chromatography on silica gel (eluent $CH_2Cl_2:CH_3OH=95:5$).

By crystallization from a mixture isopropanol:diethyl ether, S-(N,N-dimethylaminocarbonyl)-N-acetyl-L-cysteine methyl ester (3.6 g) was obtained.

$[\alpha]_D^{20}=-31.7°$ (c=1%, methanol). m.p. 119°–121° C.

EXAMPLE 6

Preparation of S-ethoxycarbonyl-N-acetyl-L-cysteine Ethyl Ester

By working in a similar way to that described in example 1 but by using ethoxycarbonyl chloride instead of isobutyryl chloride, S-ethoxycarbonyl-N-acetyl-L-cysteine ethyl ester was prepared.

$[\alpha]_D^{20}=-39.1°$ (c=1%, methanol). m.p. 41.5°–42.0° C.
$^1$H-NMR (200 MHz, $CDCl_3$): δ (ppm): 6.34 (d, 1H, $J_{HH}$=7.6 Hz, NH); 4.82–4.73 (m, 1H, C$\underline{H}$); 4.22 (q, 2H, $J_{HH}$=7.1 Hz, SCOOC$\underline{H}_2$); 4.16 (q, 2H, $J_{HH}$=7.1 Hz, COO—C$\underline{H}_2$); (AB portion of an ABX system: $v_A$=3.36, $v_B$=3.26; $J_{AB}$=14.4 Hz, $J_{AX}$=4.5 Hz, $J_{BX}$=6.0 Hz, SC$\underline{H}_2$); 1.97 (s, 3H, COC$\underline{H}_3$); 1.24 (t, 3H, $CH_2C\underline{H}_3$); 1.25 (t, 3H, $CH_2C\underline{H}_3$).

EXAMPLE 7

Preparation of S-propionyl-N-acetyl-L-cysteine Isopropyl Ester

By working in a similar way to that described in example 2 but by using propionyl chloride instead of isobutyryl chloride, S-propionyl-N-acetyl-L-cysteine isopropyl ester was prepared.

$[\alpha]_D^{20}=-27.7°$ (c=1%, methanol). m.p. 54°–55° C.
$^1$H-NMR (200 MHz, DMSO-$d_6$): δ (ppm): 6.27 (broad signal, 1H, NH); 4.98 (m, 1H, COOH); 4.67 (m, 1H, C$\underline{H}$—$CH_2$); 3.41–3.23 (m, 2H, SC$\underline{H}_2$); 2.54 (q, 2H, $J_{HH}$=7.5 Hz, SCOC$\underline{H}_2$); 1.96 (s, 3H, COC$\underline{H}_3$); 2.45 [d, 6H, $J_{HH}$=6.2 Hz, CH(C$\underline{H}_3$)$_2$]; 1.13 (T, 3H, $CH_2$—C$\underline{H}_3$).

EXAMPLE 8

In Vitro Evaluation of Transcorneal Permeability

The evaluation of the permeability of the compounds of formula I and of N-acetyl-L-cysteine through the cornea was carried out according to the experimental model described by Camber [Acta Pharm. Suec., 22, 335–342, (1985)].

Pig corneae were used within 1–2 hours from animals' death.

The corneae were removed with about 2 mm of sclera and put on perfusion cells.

The receiving as well as the donor compartment of the cells were filled with 6 ml and 1 ml, respectively, of Glutathione Bicarbonate Ringer's (GBR) solution, previously warmed at 35° C.

During the test the cells were kept at 34°–35° C. and the solution contained in the two compartments were kept under flow of a mixture 95% $O_2$ and 5% $CO_2$.

The solution in the donor compartment was, then, substituted with 1 ml of GBR solution, saturated with the mixture $O_2$—$CO_2$, containing the compound to be tested (30 μmoles).

A specimen of 600 μl every 40 minutes for a total period of 4 hours was withdrawn from the receiving compartment and immediately substituted with an equal volume of GBR solution.

The samples were at once analyzed by HPLC.

The transcorneal crossing of the unmodified compounds as well as of the eventual hydrolyzed products was evaluated.

The obtained values were corrected (+10%) in order to counterbalance the volume which was removed and substituted with GBR solution every withdrawal time.

For illustrative purpose, we reported the data of transcorneal permeability of the following representative compounds of formula I:
Compound A—S-isobutyryl-N-acetyl-L-cysteine ethyl ester
Compound B—S-(N,N-dimethylaminocarbonyl)-N-acetyl-L-cysteine methyl ester
Compound C—N-acetyl-L-cysteine ethyl ester
Compound D—N-acetyl-L-cysteine isopropyl ester
Compound E—S-propionyl-N-acetyl-L-cysteine ethyl ester
Compound F—S-ethoxycarbonyl-N-acetyl-L-cysteine ethyl ester
Compound G—S-propionyl-N-acetyl-L-cysteine isopropyl ester As reference compound, N-acetyl-L-cysteine (NAC) was used.

The amounts of compounds of formula I and of NAC passing through pig cornea are reported on the following table.

TABLE 1

Average permeated amount (total nmoles ± S.E.) of compound A, compound B, compound C, compound D, compound E, compound F, compound G and NAC through pig cornea. The donor compartment contained 30 μmoles.

| Time (minutes) | Compound | | | |
|---|---|---|---|---|
| | A | B | C | D |
| 0 | 0.0 | 0.0 | 0.0 | 0.0 |
| 40 | 472.6 ± 189.3 | 12.1 ± 0.1 | 224.7 ± 59.3 | 443.0 ± 127.6 |
| 80 | 1458.8 ± 316.9 | 120.8 ± 24.2 | 1116.3 ± 251.3 | 1828.3 ± 195.2 |
| 120 | 2403.8 ± 232.6 | 310.1 ± 60.4 | 2586.6 ± 460.0 | 3495.7 ± 214.8 |
| 160 | 3414.9 ± 110.2 | 435.0 ± 88.6 | 4507.5 ± 811.9 | 4904.3 ± 341.7 |
| 200 | 3830.2 ± 764.2 | 716.9 ± 136.9 | 6600.2 ± 1191.2 | 5489.4 ± 376.6 |
| 240 | 4132.3 ± 930.8 | 747.3 ± 213.5 | 8810.0 ± 1582.2 | 6403.2 ± 587.9 |

| Time (minutes) | Compound | | | |
|---|---|---|---|---|
| | E | F | G | NAC |
| 0 | 0.0 | 0.0 | 0.0 | 0.0 |
| 40 | 134.6 ± 25.7 | 452.9 ± 23.3 | 193.0 ± 9.5 | 0.0 |

TABLE 1-continued

Average permeated amount (total nmoles ± S.E.) of compound A, compound B, compound C, compound D, compound E, compound F, compound G and NAC through pig cornea. The donor compartment contained 30 μmoles.

| 80  | 486.4 ± 71.1   | 1091.3 ± 37.5  | 721.5 ± 41.1  | 0.0 |
| --- | -------------- | -------------- | ------------- | --- |
| 120 | 803.0 ± 44.5   | 1830.7 ± 95.2  | 1312.9 ± 66.6 | 0.0 |
| 160 | 1105.7 ± 60.7  | 2499.6 ± 124.3 | 1637.9 ± 89.2 | 0.0 |
| 200 | 1205.3 ± 134.7 | 2922.5 ± 188.0 | 1862.4 ± 37.9 | 0.0 |
| 240 | 1256.8 ± 118.9 | 3402.0 ± 358.9 | 2099.2 ± 72.8 | 0.0 |

The lag time and the absolute permeability coefficient of the compounds of formula I were calculated from the values of transcorneal crossing and compared with the literature values of some drugs used for topical ophthalmic preparations but not for the treatment of cataract.

The obtained values are reported in the following table.

TABLE 2

Absolute permeability coefficient and lag time of compound A, compound B, compound C, compound D, compound E, compound F and compound G compared with the literature values of dexamethasone, hydrocortisone and pilocarpine.

| Compound | Permeability coefficient (cm/s) × 10⁶ average (S.E.) | Lag time (minutes) |
| --- | --- | --- |
| A | 10.2 (2.1) | 20.7 |
| B | 0.8 (1.3) | 20.0 |
| C | 20.7 (4.7) | 71.6 |
| D | 16.2 (2.6) | 28.4 |
| E | 5.02 (0.65) | 28.9 |
| F | 7.34 (1.8) | 21.1 |
| G | 5.86 (1.3) | 26.2 |
| dexamethasone[a] | 0.6 (0.1) | — |
| hydrocortisone[b] | 4.7 (0.1) | 83 |
| pilocarpine[b] | 6.6 (0.1) | 68 |

Notes to the table
[a] data reported by Camber O., Edman P., Int. J. Pharm., 39, 229–234, (1987)
[b] data reported by Camber O., Acta Pharm. Suec., 22. 335–342, (1985).

The data reported in table 2 clearly show how the compounds from A to G have permeability coefficient and lag time suitable for the practical topical treatment of eye diseases.

EXAMPLE 9

Specific example of topical pharmaceutical compositions are reported in the following table 3 (component amounts expressed as percentage w/w).

| | COMPOSITION | | | | | | | | | |
| --- | --- | --- | --- | --- | --- | --- | --- | --- | --- | --- |
| | 1[a] | 2[a] | 3[a] | 4[a] | 5[a] | 6[a] | 7[a] | 8 | 9 | 10 |
| Compound I | 0.5 | 0.5 | 0.5 | 0.5 | 0.5 | 0.5 | 0.5 | 0.5 | 0.5 | 0.5 |
| EDTA Na₂ | 0.1 | 0.1 | 0.1 | 0.1 | 0.1 | 0.1 | 0.1 | 0.1 | 0.1 | 0.1 |
| PEG (Polyethyleneglycol) | 5.0 | — | — | — | — | — | — | 5.0 | — | — |
| Polysorbate 20 | — | — | — | — | — | — | 3.0 | — | — | — |
| Glucose | — | 4.0 | — | — | — | — | — | — | — | — |
| PVA (Polyvinyl alcohol) | — | — | 4.0 | — | — | — | — | — | 4.0 | — |
| PVP (Polyvinyl pyrrolidone) | — | — | — | 1.0 | — | — | — | — | — | 1.0 |
| Hydroxypropylmethylcellulose | — | — | — | — | 0.3 | — | — | — | — | — |
| Poloxamer 124 | — | — | — | — | — | 9.0 | — | — | — | — |
| Benzalkonium chloride | 0.01 | 0.01 | 0.01 | 0.01 | 0.01 | 0.01 | — | — | 0.01 | 0.01 |
| Thimerosal | — | — | — | — | — | — | 0.1 | 0.1 | — | — |
| Sodium sulfite | — | — | — | — | — | — | 0.1 | — | — | — |
| Ascorbic acid | — | — | — | — | — | — | — | 0.01 | — | — |
| Citric acid | — | — | — | — | — | — | — | 5.9 | 5.9 | 5.9 |
| Sodium phosphate dibasic dodecahydrate | — | — | — | — | — | — | — | 0.37 | 0.37 | 0.37 |
| H₂O q.s. to | 100 | 100 | 100 | 100 | 100 | 100 | 100 | 100 | 100 | 100 |

Note to the table:
[a] composition containing NaOH or HCl q.s. to about pH 7 and NaCl q.s. to isotonicity (about 287 mOsm).

What we claim is:

1. A method for treating cataract, comprising:

topically administering to an eye of a patient having cataract a therapeutic effective amount of a compound of formula I

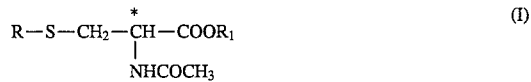

wherein R is a hydrogen atom or $R_2CO$ wherein $R_2$ is a linear or branched $C_1$–$C_4$ alkyl group, a $C_1$–$C_3$ dialkylamino group, a $C_1$–$C_3$ alkoxy group optionally substituted by a phenyl or a phenyl; $R_1$ is a linear or branched $C_1$–$C_3$ alkyl group or a benzyl; and the carbon atom marked by the asterisk has the configuration of L-cysteine.

* * * * *